United States Patent
Watanabe et al.

(10) Patent No.: US 11,730,684 B2
(45) Date of Patent: Aug. 22, 2023

(54) CLEANSING COMPOSITION

(71) Applicant: SHISEIDO COMPANY, LTD., Tokyo (JP)

(72) Inventors: Kei Watanabe, Kanagawa (JP); Takashi Meno, Kanagawa (JP)

(73) Assignee: SHISEIDO COMPANY, LTD., Tokyo (JP)

(*) Notice: Subject to any disclaimer, the term of this patent is extended or adjusted under 35 U.S.C. 154(b) by 73 days.

(21) Appl. No.: 16/342,872

(22) PCT Filed: Sep. 25, 2017

(86) PCT No.: PCT/JP2017/034551
§ 371 (c)(1),
(2) Date: Apr. 17, 2019

(87) PCT Pub. No.: WO2018/074149
PCT Pub. Date: Apr. 26, 2018

(65) Prior Publication Data
US 2019/0247286 A1 Aug. 15, 2019

(30) Foreign Application Priority Data
Oct. 19, 2016 (JP) ................ 2016-205463

(51) Int. Cl.
| | |
|---|---|
| A61K 8/04 | (2006.01) |
| A61Q 1/14 | (2006.01) |
| A61K 8/46 | (2006.01) |
| A61K 8/44 | (2006.01) |
| A61K 8/49 | (2006.01) |
| A61K 8/86 | (2006.01) |
| A61K 8/37 | (2006.01) |
| A61K 8/31 | (2006.01) |
| A61K 8/58 | (2006.01) |
| A61K 8/34 | (2006.01) |
| A61K 8/39 | (2006.01) |
| A61K 8/06 | (2006.01) |
| A61Q 19/10 | (2006.01) |
| C11D 1/94 | (2006.01) |
| A61K 8/89 | (2006.01) |
| C11D 1/18 | (2006.01) |
| C11D 1/72 | (2006.01) |
| C11D 1/29 | (2006.01) |

(52) U.S. Cl.
CPC .............. A61K 8/046 (2013.01); A61K 8/062 (2013.01); A61K 8/31 (2013.01); A61K 8/345 (2013.01); A61K 8/37 (2013.01); A61K 8/375 (2013.01); A61K 8/39 (2013.01); A61K 8/44 (2013.01); A61K 8/442 (2013.01); A61K 8/46 (2013.01); A61K 8/463 (2013.01); A61K 8/466 (2013.01); A61K 8/4946 (2013.01); A61K 8/585 (2013.01); A61K 8/86 (2013.01); A61K 8/89 (2013.01); A61Q 1/14 (2013.01); A61Q 19/10 (2013.01); C11D 1/94 (2013.01); A61K 2800/596 (2013.01); C11D 1/18 (2013.01); C11D 1/29 (2013.01); C11D 1/72 (2013.01)

(58) Field of Classification Search
CPC . A61K 8/04; A61K 8/046; A61K 8/44; A61K 8/46; A61K 8/89; A61K 8/463; A61K 8/466; A61K 8/442; A61K 8/4946; A61K 8/86; A61K 8/37; A61K 8/31; A61K 8/585; A61K 8/345; A61K 8/39; A61K 8/375; A61K 8/062; A61K 2800/596; A61K 2800/5422; A61K 2800/5428; A61K 2800/30; A61Q 19/10; A61Q 1/14; C11D 1/94; C11D 1/18; C11D 1/72; C11D 1/29; C11D 1/722; C11D 1/90
See application file for complete search history.

(56) References Cited

U.S. PATENT DOCUMENTS

| | | | |
|---|---|---|---|
| 5,294,444 A | * | 3/1994 | Nakamura ............. A61K 8/068 424/401 |
| 5,389,304 A | | 2/1995 | Repinec, Jr. et al. |
| 5,942,238 A | | 8/1999 | Mcatee et al. |
| 5,977,037 A | | 11/1999 | Giret et al. |

(Continued)

FOREIGN PATENT DOCUMENTS

| | | |
|---|---|---|
| EP | 0 684 982 A1 | 12/1995 |
| EP | 8 684 982 A1 | 12/1995 |

(Continued)

OTHER PUBLICATIONS

Google Patents translation of JP-2016050196-A (Year: 2016).*
Google Patents translation of WO-2016098649-A1 (Year: 2016).*
Google Patents translation of JP-2005306752-A 2005 (Year: 2005).*
WO2015190505A1—Google Patents translation (Year: 2015).*
EP 17861973.0, Extended European ISR and Written Opinion dated May 4, 2020, 18 pages—English.
SG 11201903471Q, ISR and Written Opinion dated Apr. 28, 2020, 9 pages—English.
CN 201780063861.6—Chinese Office Action dated Dec. 7, 2020, 7 pages—Chinese, 10 pages—English.

(Continued)

Primary Examiner — Angela C Brown-Pettigrew
Assistant Examiner — Preeti Kumar
(74) Attorney, Agent, or Firm — Andrew F. Young; Nolte Lackenbach Siegel

(57) ABSTRACT

Provided is a detergent composition that contains (A) 2-17.5 mass % of an anionic surfactant, (B) 1-17.5 mass % of an amphoteric surfactant, (C) 2.5-17 mass % of a hydrophilic non-ionic surfactant and (D) 0.2-5 mass % of an oily component. However, the detergent composition does not contain substantial amounts of fatty acid monoglycerol esters and fatty acid monoalkyl monoglyceryl ethers having alkyl groups or acyl groups having 9 or more carbon atoms. The detergent composition does not contain substantial amounts of fatty acid diglycerol esters or fatty acid monoalkyl diglyceryl ethers which have alkyl groups or acyl groups having 8 or more carbon atoms.

7 Claims, No Drawings

(56) References Cited

U.S. PATENT DOCUMENTS

| | | | | |
|---|---|---|---|---|
| 6,040,347 A | * | 3/2000 | Cupferman | A61K 31/08 514/723 |
| 6,267,985 B1 | * | 7/2001 | Chen | A61K 9/0095 424/43 |
| 6,350,460 B1 | * | 2/2002 | Andrews | A61K 8/02 424/401 |
| 6,946,139 B2 | * | 9/2005 | Henning | A61K 8/03 424/400 |
| 7,915,208 B2 | * | 3/2011 | Roso | A61Q 19/10 510/130 |
| 8,119,582 B2 | * | 2/2012 | Roso | C11D 3/221 510/130 |
| 8,476,318 B2 | * | 7/2013 | Schmaus | A61K 8/06 514/546 |
| 8,513,174 B2 | * | 8/2013 | Araki | C11D 9/225 510/122 |
| 8,741,363 B2 | * | 6/2014 | Albrecht | A61Q 1/14 424/757 |
| 2003/0032573 A1 | | 2/2003 | Tanner et al. | |
| 2005/0143269 A1 | | 6/2005 | Wei et al. | |
| 2009/0048132 A1 | | 2/2009 | Paul et al. | |
| 2009/0062406 A1 | * | 3/2009 | Loeffler | A61Q 5/02 514/785 |
| 2015/0141508 A1 | | 5/2015 | Klug et al. | |
| 2019/0247286 A1 | * | 8/2019 | Watanabe | A61K 8/442 |

FOREIGN PATENT DOCUMENTS

| | | | | |
|---|---|---|---|---|
| EP | 2 742 976 A1 | | 6/2014 | |
| GB | 2 245 281 A | | 1/1992 | |
| GB | 2 288 812 A | | 11/1995 | |
| GB | 2 297 762 A | | 8/1996 | |
| JP | 6-157253 | | 6/1994 | |
| JP | 11-43698 | | 2/1999 | |
| JP | 2000-86455 | | 3/2000 | |
| JP | 2000-336019 | | 12/2000 | |
| JP | 2001-172668 | | 6/2001 | |
| JP | 2004-292387 | | 10/2004 | |
| JP | 2005306752 A | * | 11/2005 | |
| JP | 4831609 B | | 12/2007 | |
| JP | 2010/106032 | | 5/2010 | |
| JP | 2010-222323 | | 10/2010 | |
| JP | 2011-132221 | | 7/2011 | |
| JP | 2013-144645 | | 7/2013 | |
| JP | 2013-155332 | | 8/2013 | |
| JP | 2016050196 A | * | 4/2016 | A61Q 19/00 |
| JP | 2016-205463 | | 10/2016 | |
| WO | WO 99/03968 | | 1/1999 | |
| WO | WO 2005/023975 A1 | | 3/2005 | |
| WO | WO-2015190505 A1 | * | 12/2015 | A61K 8/67 |
| WO | WO-2016098649 A1 | * | 6/2016 | A61Q 5/12 |
| WO | PCT/JP2017/34551 | | 9/2017 | |

OTHER PUBLICATIONS

CPCH1960444P, Household Cleaning, Common Evidence I, 4 pages—Chinese, 3 pages—English.

PCT/JP2017/34551 ISR and Written Opinion dated Dec. 12, 2017, 11 Pages—Japanese; 16 pages—English.

Development of Make-up Removers Consisting of a Bicontinuous Microemulsion, Journal of Scoeity Cosmetic Chemsits Japan, 2012, vol. 46, No. 2, pp. 93-100 (Kamada, Miho, et al.).

* cited by examiner

CLEANSING COMPOSITION

CROSS REFERENCE TO RELATED APPLICATIONS

This application is based upon and claims the benefit of the priority of PCT/JP2017/034551 filed Sep. 25, 2017, the entire contents of which are incorporated herein by reference, which in turn claims the priority of Japanese Patent Application No. 2016-205463 (filed Oct. 19, 2016), the disclosure of which is incorporated herein by reference.

FIGURE SELECTED FOR PUBLICATION

NA

TECHNICAL FIELD

The present disclosure relates to a cleansing (detergent) composition. For example, the present disclosure relates to a cleansing composition applicable to the skin.

BACKGROUND ART

Patent Literature 1 discloses a cleansing composition applicable to makeup (cosmetic) removal. The cleansing composition disclosed in Patent Literature 1 includes (A) an amphoteric surfactant, (B) an anionic surfactant, (C) a monoglycerin derivative and/or a diglycerin derivative having a specific structure, (D) at least one type of compound selected from the group consisting of dihydric alcohols including ethylene glycol, propylene glycol, isopropylene glycol, 1,3-butylene glycol, dipropylene glycol, polyethylene glycol, and polypropylene glycol, and (E) water, wherein the average value of the ratio between the inorganic value and the organic value (i.e., inorganic value/organic value) of each component (C) is within the range from 0.8 to 1.5, and the cleansing composition is in a bicontinuous microemulsion phase at 25° C.

Patent Literature 2 discloses an aqueous liquid cleansing composition that can be employed in a foam-dispensing pump container (pump foamer). The aqueous liquid cleansing composition disclosed in Patent Literature 2 includes: (A) at least one type of cleansing surfactant selected from higher fatty acid salts and/or betaine-type amphoteric surfactants; (B) a polyoxyethylene glyceryl fatty acid ester or a polyoxyethylene sorbitol fatty acid ester having a HLB of 8 to 12; (C) diethylene glycol laurate; (D) 2 to 10% by mass of an ester oil that is made from a $C_{12-18}$ higher fatty acid and a $C_{2-6}$ monohydric alcohol and is in a liquid state at 25° C.; and (E) water.

CITATION LIST

Patent Literature

Patent Literature 1: Japanese Patent No. 4831609B
Patent Literature 2: Japanese Unexamined Patent Publication No. 2011-132221A

SUMMARY OF INVENTION

Technical Problem

The following analysis is provided from the perspective of the present disclosure.

The cleansing compositions disclosed in Patent Literatures 1 and 2 are insufficient in terms of cleansing capability with respect to waterproof-type makeup.

An excellent foaming ability is also demanded of cleansing compositions in order to offer a comfortable feel upon use in addition to enhancing cleansing ability thereof.

Thus, there is a demand for cleansing compositions providing an excellent foaming ability along with excellent cleansing ability.

Solution to Problem

According to a first aspect of the present disclosure, it is provided that a cleansing composition comprises (A) 2 to 17.5% by mass of an anionic surfactant, (B) 1 to 17.5% by mass of an amphoteric surfactant, (C) 2.5 to 17% by mass of a nonionic surfactant, and (D) 0.2 to 5% by mass of an oily component. Whereas, the cleansing composition does not contain a practical and meaningful amount of a compound represented by Chem. 1 or Chem. 2 below.

[Chem.1]

(Any one of $R^1$, $R^2$, and $R^3$ is an alkyl group or acyl group having nine or more carbon atoms, and the other two are hydrogen atoms (—H).)

[Chem.2]

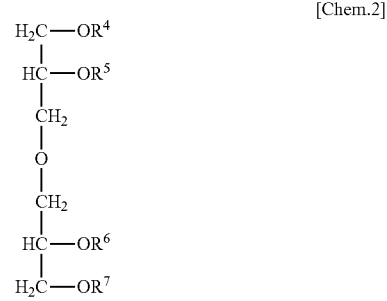

(Any one of $R^4$, $R^5$, $R^6$, and $R^7$ is an alkyl group or acyl group having eight or more carbon atoms, and the other three are hydrogen atoms (—H).)

Advantageous Effects of Invention

The cleansing composition of the present disclosure can achieve providing an excellent cleansing. The cleansing composition of the present disclosure can also achieve providing excellent foaming (lathering).

DESCRIPTION OF EMBODIMENTS

Preferred modes according to the aforementioned aspects of the disclosure are described below.

According to a preferred mode of the first aspect, a ratio of a mass of the component (A) to a total mass of the component (A) and the component (B) is in the range of 0.1 to 0.9.

According to a preferred mode of the first aspect, a ratio of a total mass of the component (A) and the component (B) to a total mass of the component (A), the component (B), the component (C), and the component (D) is in the range of 0.35 to 0.9.

According to a preferred mode of the first aspect, the cleansing composition further comprises (E) 0.4 to 5% by mass of a foaming agent.

According to a preferred mode of the first aspect, the component (E) includes at least one compound represented by Chem. 3 below:

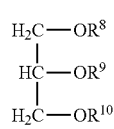

[Chem.3]

(Any one of $R^8$, $R^9$, and $R^{10}$ is an alkyl group or acyl group having eight or fewer carbon atoms, and the other two are hydrogen atoms (—H).)

According to a preferred mode of the first aspect, the cleansing composition further comprises (F) 60 to 85% by mass of water.

According to a preferred mode of the first aspect, the component (A) includes a polyoxyethylene alkyl ether sulfate and/or an acyl methyl taurate.

According to a preferred mode of the first aspect, the component (B) is a betaine-type surfactant.

According to a preferred mode of the first aspect, the component (C) has an HLB of 9 to 14.

According to a preferred mode of the first aspect, the component (C) is a polyoxyethylene glyceryl fatty acid ester.

According to a preferred mode of the first aspect, the cleansing composition includes no bicontinuous phase.

According to a preferred mode of the first aspect, the cleansing composition is applicable using a pump foamer without using a high-pressure gas.

According to a preferred mode of the first aspect, the cleansing composition is used as a makeup cleansing agent.

A cleansing composition according to a first embodiment of the present disclosure is described below. The cleansing composition of the present disclosure can be employed, for example, for cleansing the skin, and particularly, can be employed for cleansing cosmetics (makeup) on the skin.

In the present disclosure, "practical amount" refers to an amount that can provide any function/effect achieved by the addition of the compound in question.

In the following description, POE is an abbreviation of polyoxyethylene, POP is an abbreviation of polyoxypropylene, and the number in parentheses following POE or POP indicates the average number of moles of POE groups or POP groups added in the respective compound.

The cleansing composition of the present disclosure includes: (A) an anionic surfactant; (B) an amphoteric surfactant; (C) a nonionic surfactant; and (D) an oily component. The cleansing composition of the present disclosure does not have to include a bicontinuous phase.

(A) Anionic Surfactant:

Examples of the anionic surfactants that may be used may include fatty acid soap (such as sodium laurate, and sodium palmitate); higher alkyl sulfate ester salt (such as sodium lauryl sulfate, and potassium lauryl sulfate); alkyl ether sulfate ester salt (such as POE-lauryl sulfate trietha- nolamine, and sodium POE-lauryl sulfate); N-acyl sarcosinic acid (such as sodium lauroyl sarcocinate); higher fatty acid amide sulfonate (such as sodium N-stearoyl-N-methyltaurate, sodium N-myristoyl-N-methyltaurate, sodium methyl cocoyl taurate, and sodium laurylmethyl taurate); phosphate ester salt (sodium POE-oleylether phosphate, and POE-stearylether phosphate); sulfosuccinate (such as sodium di-2-ethylhexyl sulfosuccinate, sodium monolauroyl monoethanolamide polyethylene sulfosuccinate, and sodium lauryl polypropylene glycol sulfosuccinate); alkylbenzene sulfonate (such as sodium linear dodecylbenzene sulfonate, triethanolamine linear dodeyl-benzene sulfonate, and linear dodecylbenzene sulfonate); higher fatty acid ester sulfate ester salt (such as sodium hydrogenated gryceryl cocoate sulfate); N-acyl glutamate (such as monosodium N-lauroyl glutamate, disodium N-stearoyl glutamate, and monosodium N-myristoyl-L-glutamate); sulfonated oil (such as Turkey red oil); POE-alkyl ether carboxylic acid; POE-alkyl aryl ether carboxylate; α-olefine sulfonate; higher fatty acid ester sulfonate; secondary alcohol sulfate ester salt; higher fatty acid alkylolamide sulfate ester salt; sodium lauroyl monoethanolamide succinate; N-palmitoyl asparaginate ditriethanolamine; sodium casein; and the like.

From the viewpoint of cleansing ability and foaming ability, it is preferred that the anionic surfactant includes, for example, a polyoxyethylene alkyl ether sulfate and/or an acyl methyl taurine salt.

The content by percentage of the anionic surfactant to the mass of the composition is preferably 2% by mass or greater, more preferably 3% by mass or greater, even more preferably 4% by mass or greater. If the content by percentage of the anionic surfactant is less than 2% by mass, cleansing ability will deteriorate, and also the transparency of the composition becomes inferior. Preferably, the content by percentage of the anionic surfactant to the mass of the composition is 17.5% by mass or less, 17% by mass or less, 15% by mass or less, 13% by mass or less, or 11% by mass or less. Excellent cleansing ability and foaming ability can be achieved in this range.

(B) Amphoteric Surfactant:

Examples of the amphoteric surfactant that may be used may include: imidazoline-based amphoteric surfactant (such as sodium 2-undecyl-N,N,N-(hydroxyethylcarboxymethyl)-2-imidazoline and 2-cocoyl-2-imidazolinium hydroxide-1-carboxyethyloxy disodium salt); and betaine-based surfactant (such as 2-heptadecyl-N-carboxymethyl-N-hydroxyethyl imidazolinium betaine, lauryl dimethylaminoacetic acid betaine, alkyl betaine, amidobetaine, and sulfobetaine).

From the viewpoint of cleansing ability and foaming ability, it is preferred that the amphoteric surfactant is a betaine-based surfactant. Preferably, the amphoteric surfactant includes, for example, cocamidopropyl betaine and/or imidazolinium betaine.

The content by percentage of the amphoteric surfactant to the mass of the composition is preferably 1% by mass or greater, more preferably 1.5% by mass or greater, even more preferably 2% by mass or greater. If the content by percentage of the amphoteric surfactant is less than 1% by mass, the transparency of the composition becomes inferior. Preferably, the content by percentage of the amphoteric surfactant to the mass of the composition is 17.5% by mass or less, 17% by mass or less, 15% by mass or less, 13% by mass or less, 11% by mass or less, 9% by mass or less, or 7% by mass or less. Excellent cleansing ability and foaming ability can be achieved in this range.

(C) Nonionic Surfactant:

The nonionic surfactant may include a polyoxyalkylene glyceryl fatty acid ester, for example.

Examples of the nonionic surfactants that may be used may include POE sorbitan fatty acid ester (such as POE sorbitan monooleate, POE sorbitan monostearate, POE sorbitan monooleate, POE sorbitan tetraoleate); POE sorbit fatty acid ester (such as POE sorbit monolaurate, POE sorbit monooleate, POE sorbit pentaoleate, POE sorbit monostearate), POE glyceryl fatty acid ester (such as POE monooleate such as POE glyceryl monostearate, POE glyceryl monoisostearate, POE glyceryl triisostearate); POE fatty acid ester (such as POE distearate, POE monodioleate, ethyleneglycol distearate); POE alkyl ether (such as POE lauryl ether, POE oleyl ether, POE stearyl ether, POE behenyl ether, POE-2-octyldodecyl ether, POE cholestanol ether); puluronic type (such as Puluronic), POE/POP alkyl ethers (such as POE/POP cetyl ether, POE/POP 2-decyltetradecyl ether, POE/POP monobutyl ether, POE/POP hydrogenated lanoline, POE/POP glycerin ether); tetra POE/tetra POP ethylenediamine condensation products (such as Tetronic); POE castor oil hydrogenated castor oil derivative (such as POE caster oil, POE hydrogenated caster oil, POE hydrogenated caster oil monoisostearate, POE hydrogenated castor oil triisostearate, POE hydrogenated caster oil monopyroglutamate monoisostearate diester, POE hydrogenated oil maleate); POE beeswax/lanoline derivative (such as POE sorbitol beeswax); alkanolamide (such as coconut oil fatty acid diethanolamide, lauric acid monoethanolamide, fatty acid isopropanolamide); POE propyleneglycol fatty acid ester; POE alkyl amines; POE fatty acid amide; sucrose fatty acid ester; alkylethoxydimethylamine oxide; trioleyl phosphoric acid and the like.

From the viewpoint of cleansing ability and foaming ability, it is preferred that the nonionic surfactant includes polyoxyethylene glyceryl isostearate, for example. The HLB of the nonionic surfactant is preferably 9 or greater, more preferably 10 or greater. If the HLB is less than 9, the transparency of the composition becomes inferior. The HLB of the nonionic surfactant is preferably 14 or less, more preferably 13 or less. If the HLB is greater than 14, cleansing ability will deteriorate, and also foam quality by a pump foamer will deteriorate.

Preferably, the cleansing composition of the present disclosure includes neither a glycerin mono-fatty acid ester nor a monoalkyl monoglyceryl ether. Herein, glycerin mono-fatty acid esters and monoalkyl monoglyceryl ethers are compounds represented by the following Chem. 4 and Chem. 5. If the composition includes a compound represented by Chem. 4, the cleansing composition becomes opaque. Further, if the composition includes a compound represented by Chem. 4 and Chem. 5, foaming ability thereof becomes poor. Moreover, if the composition includes the compound represented by Chem. 5, the composition becomes sticky on the use thereof.

[Chem.4]

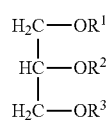

(In the formula, any one of $R^1$, $R^2$, and $R^3$ is an alkyl group or acyl group having nine or more carbon atoms and the other two are hydrogen atoms (—H).)

[Chem.5]

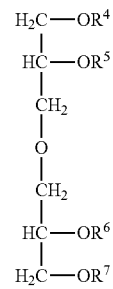

(In the formula, any one of $R^4$, $R^5$, $R^6$, and $R^7$ is an alkyl group or acyl group having eight or more carbon atoms, and the other three are hydrogen atoms (—H).)

The content by percentage of the nonionic surfactant to the mass of the composition is preferably 2.5% by mass or greater, more preferably 3% by mass or greater, even more preferably 4% by mass or greater, further more preferably 5% by mass or greater. If the content of the nonionic surfactant is less than 2.5% by mass, cleansing ability becomes poor. Note, however, that in cases where the later-described ionicity ratio is 0.8 or greater, the content by percentage of the nonionic surfactant to the mass of the composition may be 2% by mass or greater, preferably 3% by mass or greater. Preferably, the content by percentage of the nonionic surfactant to the mass of the composition is 17% by mass or less, 15% by mass or less, 13% by mass or less, 11% by mass or less, 9% by mass or less, or 7% by mass or less.

(D) Oily Component:

Examples of the oily component that may be used include liquid oils, solid fats, waxes, hydrocarbons, higher fatty acids, higher alcohols, synthetic ester oils, and silicone oils.

Examples of the liquid fat that may be used may include avocado oil, camellia oil, turtle oil, macadamia nut oil, corn oil, mink oil, olive oil, rapeseed oil, egg yolk oil, sesame oil, par chic oil, wheat germ oil, southern piece oil, castor oil, linseed oil, safflower oil, cotton seed oil, perilla oil, soybean oil, groundnut oil, brown real oil, torreya oil, rice bran oil, Chinese tung oil, Japanese tung oil, jojoba oil, germ oil, triglycerol, and the like.

Examples of the solid fat that may be used may include cacao butter, coconut oil, horse fat, hydrogenated coconut oil, palm oil, beef tallow, sheep tallow, hydrogenated beef tallow, palm kernel oil, lard, beef bones fat, Japan wax kernel oil, hardened oil, hoof oil, Japan wax, hydrogenated caster oil, and the like.

Examples of the waxes that may be used may include beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl ester, hexyl laurate, reduced lanolin, jojoba wax, hardened lanolin, shellac wax, POE lanolin alcohol ether, POE lanolin alcohol acetate, POE cholesterol ether, lanolin fatty acid polyethylene glycol, POE hydrogenated lanolin alcohol ether, and the like.

Examples of the hydrocarbon oils that may be used may include lsiquid paraffin, ozocerite, squalane, pristane, paraffin, ceresin. squalene, vaseline, microcrystalline wax, and the like.

Examples of the higher fatty acid that may be used may include lauric acid, myristic acid, palmitic acid, stearic acid, behenic acid, oleic acid, undecylenic acid, tallic acid, isostearic acid, linoleic acid, linolenic acid, eicosapentaenoic acid (EPA), docosahexaenoic acid (DHA) and the like.

Examples of the higher alcohol that may be used may include linear alcohol (such as lauryl alcohol, cetyl alcohol, stearyl alcohol, behenyl alcohol, myristyl alcohol, oleyl alcohol, and cetostearyl alcohol); branched-chain alcohol (such as monostearylglycerin ether (batyl alcohol), 2-decyltetradecinol, lanolin alcohol, cholesterol, phytosterol, hexyldodecanol, isostearyl alcohol, and octyldodecanol) and the like.

Examples of the synthesis ester oils that may be used may include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, dipenta erythritol fatty acid ester, N-alkyl glycol monoisostearate, neopentyl glycol dicaprate, diisostearyl malate, glyceryl di-2-heptyl undecanoate, trimethyrol propane tri-2-ethyl hexanoate, trimethyrol propane triisostearate, pentaerythritol tetra-2-ethyl hexanoate, glyceryl tri-2-ethyl hexanoate, glyceryl trioctanoate, glyceryl triisopalmitate, trimethyrol propane triisostearate, cetyl 2-ethylhexanoate, 2-ethylhexyl palmitate, glyceryl trimyristate, glyceride tri-2-heptyl undecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, and the like.

Examples of the silicone oil that may be used include dimethylpolysiloxane, methylhydrogenpolysiloxane, methylphenylpolysiloxane, stearoxymethylpolysiloxane, polyether-modified organopolysiloxane, fluoroalkyl/polyoxyalkylene co-modified organopolysiloxane, alkyl-modified organopolysiloxane, terminal-modified organopolysiloxane, fluorine-modified organopolysiloxane, amino-modified organopolysiloxane, silicone gel, acrylic silicone, trimethylsiloxysilicic acid, silicone compounds such as silicone RTV rubber, and the like.

The content by percentage of the oily component to the mass of the composition is preferably 0.2% by mass or greater, more preferably 0.5% by mass or greater, even more preferably 1% by mass or greater. If the content is less than 0.2% by mass, cleansing ability becomes poor. The content by percentage of the oily component to the mass of the composition is preferably 5% by mass or less, more preferably 4% by mass or less. If the content is greater than 5% by mass, foaming ability becomes poor.

(E) Foaming (Lathering) Agent (Foam-Boosting Agent):

The cleansing composition of the present disclosure may further include a foaming agent (foam-boosting agent; cosurfactant) in addition to the aforementioned components. A foaming agent improves the foaming ability of the cleansing composition of the present disclosure. Examples of the foaming agent that may be used may include water-soluble polyols and/or derivatives thereof. Examples of the foaming agent may include octoxyglycerin, glyceryl isooctanoate, polyglyceryl-2 laurate, and glyceryl monooctanoate.

The foaming agent may be at least one compound selected from compounds represented by the following Chem. 6. A compound represented by the following Chem. 6 can improve foaming ability without deteriorating the transparency of the cleansing composition. If the compound includes an alkyl group or acyl group having nine or more carbon atoms as represented by the aforementioned Chem. 4, not only will appearance stability deteriorate, but also cleansing ability, foaming ability and foam quality become poor.

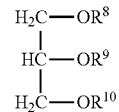

[Chem.6]

(In the formula, any one of $R^8$, $R^9$, and $R^{10}$ is an alkyl group or acyl group having eight or fewer carbon atoms, and the other two are hydrogen atoms (—H).)

The content by percentage of the foaming agent to the mass of the composition is preferably 0.4% by mass or greater, more preferably 0.5% by mass or greater, even more preferably 1% by mass or greater. The content by percentage of the foaming agent to the mass of the composition is preferably 5% by mass or less, more preferably 3% by mass or less. If the content is greater than 5% by mass, the appearance is instable.

(F) Water:

In addition to the aforementioned components, the cleansing composition of the present disclosure may further include water. For the water, it is possible to use water used for products such as makeup and quasi-pharmaceutical products, with examples including purified water, ion-exchanged water, and tap water. Depending on the purpose, the aqueous phase may further include a water-soluble alcohol.

The content by percentage of water to the mass of the composition may be 60% by mass or greater. The content by percentage of water to the mass of the composition may be 85% by mass or less. When the content by percentage of water is within the aforementioned range, the composition of the present disclosure can be employed suitably in a pump foamer.

The ratio (referred to herein as "ionicity ratio") of the total mass of (A) the anionic surfactant and (B) the amphoteric surfactant to the total mass of (A) the anionic surfactant, (B) the amphoteric surfactant, (C) the nonionic surfactant, and (D) the oily component, as represented by Math. 1 below, is preferably 0.35 or greater, more preferably 0.4 or greater, even more preferably 0.5 or greater. If the ionicity ratio is less than 0.35, foaming ability and foam quality from a pump foamer become poor. The ionicity ratio is preferably 0.9 or less. If the ionicity ratio is greater than 0.9, cleansing capability becomes poor. In Math. 1, the symbols represent the mass of the respective components.

$$\text{Ionicity ratio} = \frac{(A)+(B)}{(A)+(B)+(C)+(D)} \qquad [\text{Math. 1}]$$

The ratio (referred to herein as "anionicity ratio") of the mass of (A) the anionic surfactant to the total mass of (A) the anionic surfactant and (B) the amphoteric surfactant, as represented by Math. 2 below, is preferably 0.1 or greater, more preferably 0.15 or greater, even more preferably 0.2 or greater, even more preferably 0.3 or greater, even more preferably 0.4 or greater, even more preferably 0.5 or greater. If the ionicity ratio is less than 0.1, cleansing capability and foaming ability become poor. The ionicity ratio is preferably 0.9 or less, more preferably 0.8 or less. If the ionicity ratio is greater than 0.9, the composition will become clouded and opaque, and also, foaming ability and foam quality from a pump foamer become poor. In Math. 2, the symbols represent the mass of the respective components.

$$\text{Anionicity ratio} = \frac{(A)}{(A)+(B)} \quad \text{[Math. 2]}$$

Others:

The cleansing composition of the present disclosure may include, as appropriate and as necessary, other components—such as aqueous solvents, cationic surfactants, oleophilic nonionic surfactants, powder bodies, moisturizers, water-soluble polymers, thickeners, film-forming agents, UV absorbers, metal ion sequestering agents, amino acids, organic amines, polymer emulsions, pH adjusters, skin nutrients, vitamins, antioxidants, antioxidant aids, and perfumes—in amounts that do not inhibit the effects of the present disclosure.

Examples of aqueous solvents may include water, alcohols, and mixtures thereof.

Examples of water-soluble alcohols may include at least one type selected from lower alcohols, polyhydric alcohols, polyhydric alcohol polymers, dihydric alcohol alkyl ethers, dihydric alcohol alkyl ethers, dihydric alcohol ether esters, glycerin monoalkyl ethers, sugar alcohols, monosaccharides, oligosaccharides, polysaccharides, and derivatives of the above.

Examples of the lower alcohol may include ethanol, propanol, isopropanol, isobutyl alcohol, t-butyl alcohol, and the like.

Examples of the polyhydric alcohol may include dihydric alcohol (such as ethylene glycol, propylen glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, etc); trihydric alcohol (such as glycerin, trimethylolpropane, etc); tetrahydric alcohol (such as such as pentaerythritol such as 1,2,6-hexanetriol, etc); pentahydric alcohol (such as xylitol, etc); hexahydric alcohol (such as sorbitol, mannitol, etc); polyhydric alcohol polymer (such as diethylene glycol, dipropylene glycol, triethylene glycol, polypropylene glycol, tetraethylene glycol, diglycerin, polyethylene glycol, triglycerin, tetraglycerin, polyglycerin, etc); dihydric alcohol alkyl ethers (such as ethylene glycol monomethyl ether, ethylene glycol monoethyl ether, ethylene glycol monobutyl ether, ethylene glycol monomphenyl ether, ethylene glycol monohexyl ether, ethylene glycol mono2-methylhexyl ether, ethylene glycol isoamyl ether, ethylene glycol benzil ether, ethylene glycol isopropyl ether, ethylene glycol dimethyl ether, ethylene glycol diethyl ether, ethylene glycol dibutyl ether, etc); dihydric alcohol alkyl ethers (such as diethylene glycol monomethyl ether, diethylene glycol monoethyl ether, diethylene glycol monombutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, etc); dihydric alcohol ether ethers (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, etc); glycerin monoalkyl ether (such as chimyl alcohol, selachyl alcohol, batyl alcohol, etc); sugar alcohol (such as sorbitol, maltitol, maltotriose, mannitol, sucrose, erythritol, glucose, fructose, starch sugar, maltose, xylitose, starch sugar hydrogenated alcohol, etc); glycolide, tetrahydrofurfuryl alcohol; POE-tetrahydrofurfuryl alcohol; POP/POE-butyl ether; tripolyoxypropylene glycerin ether; POP-glycerin ether; POP-glycerin ether phosphoric acid; POP/POE-pentaerythritol ether; polyglycerin, and the like.

Examples of the monosaccharides may include at least one selected from triose (such as D-glyceryl aldehyde, dihydroxyacetone, etc); tetrose (such as D-erythrose, D-erythrulose, D-threose, erythritol, etc); pentaose (such as L-arabinose, D-xylose, L-lyxose, D-arabinose, D-ribose, D-ribulose, D-xylulose, L-xylulose, etc); hexalose (such as D-glucose, D-talose, D-psicose, D-galactose, D-fructose, L-galactose, L-mannose, D-tagatose, etc); heptose (such as aldoheptose, heplose); octose (such as octulose, etc); deoxy sugar (such as 2-deoxy-D-ribose, 6-deoxy-L-galactose, 6-deoxy-L-mannose, etc); amino sugar (such as D-glucosamine, D-galactosamine, sialic acid, amino uronic acid, muramic acid, etc); uronic acid (such as D-grucuronic acid, D-mannuronic acid, L-guluronic acid, D-garacturonic acid, L-iduronic acid, etc) and the like.

Examples of the oligosaccharide may include at least one selected from sucrose, guntianose, umbelliferose, lactose, planteose, isolignoses, α,α-trehalose, raffinose, lignoses, umbilicin, stachyose, verbascoses, and the like.

Examples of the polysaccharide may include at least one selected from cellulose, quince seed, chondroitinsulfate, starch, galactan, dermatan sulfate, glycogen, acasia gum, heparansulfate, hyaluronan, gum tragacanth, keratan sulfate, chondoroitin, xanthan gum, mucoitin sulfate, guar gum, dextran, keratosulfate, locust bean gum, succinoglycan, caronic acid, and the like.

Examples of other polyols may include at least one selected from polyoxyethylene methyl glucoside (Glucum E-10), polyoxypropylene methyl glucoside (Glucum P-10), and the like.

Examples of the cationic surfactants may include alkyltrimethyl ammonium salt (such as stearyltrimethyl ammonium chloride, lauryltrimethyl ammonium chloride); alkylpyridinium salt (such as cetylpyridinium chloride); distearyldimethyl ammonium chloride; dialkyldimethyl ammonium salt; poly (N,N'-dimethyl-3,5-methylenepiperidinium) chloride; alkyl quaternary ammonium salt; alkyldimethylbenzyl ammonium salt; alkylisoquinolinium salt; dialkylmorphonium salt; POE alkylamine; alkylamine salt; polyamine fatty acid derivative; amyl alcohol fatty acid derivative; benzalkonium chloride; benzethonium chloride, and the like.

Examples of the lipophilic nonionic surfactants may include sorbitan fatty acid ester (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2 ethylhexylate, diglycerol sorbitan tetra-2 ethylhexylate, etc); glyceryl polyglyceryl fatty acid (such as glyceryl monocotton oil fatty acid, glyceryl monoerucate, glyceryl sesquioleate, glyceryl monostearate, glyceryl α, α'-oleate pyroglutamate, glyceryl monostearate malate, etc); propylene glycol fatty acid ester (such as propylene glycol monostearate, etc); hydrogenated caster oil derivative; glyceryl alkyl ether, and the like.

The terms "powdery body" and "powder" as used herein are synonymous. Powdery bodies are not particularly limited so long as they are generally usable for makeup purposes, for example. Examples of the powder bodies may include inorganic powder (such as talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstate, magnesium, silica, zeolite, glass, barium sulfate, calcined calcium sulfate (calcined gypsum), calcium phosphate, fluorine apatite, hydroxyapatite, ceramic powder, metallic soap (such as zinc myristate, calcium palimitate, and aluminum stearate), and boron nitride, etc); organic powder (such as polyamide resin powder (nylon powder), polyethylene powder, polymethylmethacrylate powder, polystyrene powder, styrene-acrylic acid copolymer powder, benzoguanamine resin powder, poly(tetrafluroethylene) powder, and cellulose powder, silicone resin powder, silk powder, wool powder, urethane powder, etc); inorganic white family pigment (such as titanium dioxide, zinc oxide, etc); inorganic red family pigment (such as iron oxide (colcothar), iron titanate, etc); inorganic brown family pigment (such as γ-iron oxide, etc); inorganic yellow family pigment (such as yellow iron oxide, loess, etc); inorganic black family pigment (such as black iron oxide, carbon black, lower titanium oxide, etc); inorganic purple family pigment (such as manganese violet, cobalt violet, etc); inorganic green family pigment (such as chrome oxide, chrome hydroxide, cobalt titanate, etc); inorganic blue family pigment (such as ultramarine, iron blue, etc); pearl pigment (such as titanium oxide coated mica, titanium oxide coated bismuth oxychloride, titanium oxide coated talc, colored titanium oxide coated mica, bismuth oxychloride, argentine, etc); metal powder pigment (such as aluminum powder, copper powder, etc); organic pigment such as zirconium, barium, or aluminum lake (such as organic pigment such as Red No. 201, Red No. 202, Red No. 204, Red No. 205, Red No. 220, Red No. 226, Red No. 228, Red No. 405, Red No. 201, Orange No. 203, Orange No. 204, Yellow No. 205, Yellow No. 401, Blue No. 401, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1, etc); natural pigment (such as chlorophyll, β-carotene, etc), and the like.

Examples of the moisturizers may include polyethylene glycol, propylene glycol, glycerin, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile salt, dl-pyrrolidone carboxylate, alkyleneoxide derivative, short-chain soluble collagen, diglycerin (EO)PO adduct, chestnut rose extract, yarrow extract, melilot extract, and the like.

Examples of the natural water-soluble polymer may include plant-based polymer (such as gum Arabic, gum tragacanth, galactan, guar gum, locust bean gum, gum karaya, carrageenan, pectine, agar, quince seed (cydonia oblonga), algae colloid (brown algae extract), starch (rice, corn, potato, wheat), glicyrrhizic acid); microorganism based polymer (such as xanthan gum, dextran, succinoglycan, pullulan, etc), animal-based polymer (such as collagen, casein, albumin, gelatine, etc) and the like.

Examples of the semisynthetic water-soluble polymer may include starch-based polymer (such as carboxymethyl starch, methylhydroxypropyl starch, etc); cellulose-based polymer (such as methylcellulose, ethylcellulose, methylhydroxypropylcellulose, hydroxyethylcellulose, cellulose sodium sulfate, hydroxypropylcellulose, carboxymethylcellulose, sodium calboxymethyl cellulose, crystalline cellulose, cellulose powder, etc); algin acid-based polymer (such as sodium alginate, propylene glycol alginate ester, etc), and the like.

Examples of the synthetic water-soluble polymer may include vinyl based polymer (such as polyvinyl alcohol, polyvinyl methyl ether, polyvinylpyrrolidone, carboxyvinylpolymer, etc); polyoxyethylene based polymer (such as polyoxyethylenepolyoxypropylene copolymer such as polyethylene glycol 20,000, 40,000 and 60,000, etc); acrylic polymer (such as sodium polyacrylate, polyethylacrylate, polyacrylamide, etc); polyethyleneimine; cationic polymer; and the like.

Examples of the thickener may include gum Arabic, carrageenan, gum karaya, gum tragacanth, carob gum, quince seed (cydonia oblonga), casein, dextrine, gelatine, sodium pectate, sodium alginate, methylcellulose, ethylcellulose, carboxymethylcellulose (CMC), hydroxyethylcellulose, hydroxypropylcellulose, polyvinyl alcohol (PVA), polyvinyl methyl ether (PVM), polyvinylpyrrolidone (PVP), sodium polyacrylate, carboxyvinylpolymer, locust bean gum, guar gum, tamarind gum, dialkyldimethylammonium cellulose sulfate, xanthan gum, aluminium magnesium silicate, bentonite, hectorite, aluminium magnesium silicate (veegum), laponite, silicic anhydride, taurate-based synthetic polymer, acrylate-based synthetic polymer, and the like.

Examples of the film-forming agent may include an anionic film-forming agent (such as (meta)acrylic acid/(meta)acrylic acid ester copolymer, methyl vinyl ether/maleic anhydride coplymer, etc), a cationic film-forming agent (such as cationic cellulose, diallyldimethylammonium chloride polymer, diallyldimethylammonium chloride/acrylic amide copolymer, etc), a nonionc film-forming agent (such as polyvinyl alcohol, polyvinylpyrrolidone, polyvinyl acetate, polyacrylic ester copolymer, (meta)acrylamide, polymeric silicone, silicone resin, trimethylsiloxysilicate, etc), and the like.

Examples of the ultraviolet light absorbers may include benzoic acid family ultraviolet light absorber (such as p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc); anthranilic acid family ultraviolet light absorber (such as homomenthyl N-acetylanthrani late etc); salicylic acid family ultraviolet light absorber (such as amyl salicylate, menthyl salicylate, homomenthyl salicylate, octyl salicylate, phenyl salicylate, benzyl salicylate, p-isopropanolphenyl salicylate, etc); cinnamic acid family ultraviolet light absorber (such as octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxy cinnamate, etc); benzophenone family ultraviolet light absorber (such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc); 3-(4'-methylbenzylidene)-d,l-camphor and 3-benzylidene-d,l-camphor; 2-phenyl-5-methylbenzoxazol; 2,2'-hydroxy-5-methylphenylbenzotriazol, 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; 5-(3,3-dimethyl-2-norbornylidene)-3-pentane-2-one; dimorpholinopyridazinone; 2-ethylhexyl 2-cyano-3,3-diphenylacrylate; 2,4-bis-{[4-(2-ethylhexyloxy)-2-hydroxy]-phenyl}-6-(4-methoxyphenyl)-(1,3,5)-triazine, and the like.

Examples of the chelate agent may include 1-hydroxyethane-1, 1-diphosphonic acid, 1-hydroxyethane, 1-diphosphonic acid 4Na salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, trisodium hydroxyethyl ethylenediamine triacetate, and the like.

Examples of the amino acid may include neutral amino acid (such as threonine, cysteine, etc); basic amino acid (such as hydroxylysine, etc) and the like. Examples of the amino acid derivative may include sodium acyl sarcosinate (sodium lauroyl sarcosinate), acyl glutamate, sodium acyl β-alanine, glutathione, pyrrolidone carboxylate, and the like.

Examples of the organic amine may include monoethanolamine, diethanolamine, triethanolamine, morpholine, triisopropanolamine, 2-amino-2-methyl-1,3-propanediol, 2-amino-2-methyl-1-propanol, and the like.

Examples of the polymer emulsion may include acrylic resin emulsion, ethyl polyacrylate emulsion, solution of acrylic resin, polyacrylalkylester emulsion, polyvinyl acetate resin emulsion, natural rubber latex, and the like.

Examples of the pH modifier may include buffer such as lactic acid-sodium lactate, citric acid-sodium citrate, succinic acid-sodium succinate, and the like.

Examples of the vitamins may include vitamin A, B1, B2, B6, C, E and derivatives thereof, pantothenic acid and derivatives thereof, biotin, and the like.

Examples of the anti-oxidant may include tocopherols, dibutyl hydroxy toluene, butyl hydroxy anisole, and gallic acid esters, and the like.

Examples of the anti-oxidant aid may include phosphoric acid, citric acid, ascorbic acid, maleic acid, malonic acid, succinic acid, fumaric acid, cephalin, hexamethaphosphate, phytic acid, ethylenediaminetetraacetic acid, and the like.

Examples of other containable compositions may include an antiseptic agent (such as ethylparaben, butylparaben, chlorphenesin, 2-phenoxyethanol, etc); antiphlogistic (such as glycyrrhizinic acid derivatives, glycyrrhetic acid derivatives, salicylic acid derivatives, hinokitiol, zinc oxide, allantoin, etc); a skin-whitening agent (such as placental extract, saxifrage extract, arbutin, etc); various extracts (such as phellodendron bark (cork tree bark), coptis rhizome, lithospermum, peony, swertia herb, birch, sage, loquat, carrot, aloe, mallow, iris, grape, coix seed, sponge gourd, lily, saffron, cnidium rhizome, ginger, hypericum, restharrow, garlic, red pepper, citrus unshiu, Japanese angelica, seaweed, etc); an activator (such as royal jelly, photosenstizer, cholesterol derivatives, etc); a blood circulation promotion agent (such as nonylic acid vanillylamide, nicotine acid benzyl ester, nicotine acid β-butoxyethyl ester, capsaicin, zingerone, cantharides tincture, ichthammol, tannic acid, α-borneol, tocopheryl nicotinate, meso-inositol hexanicotinate, cyclandelate, cinnarizine, tolazoline, acetylcholine, verapamil, cepharanthine, γ-oryzanol, etc); an antiseborrheric agent, (such as sulfur, thianthl, etc); an anti-inflammatory agent (such as tranexamic acid, thiotaurine, hypotaurine, etc), and the like.

The composition of the present disclosure further may include, as necessary, caffeine, tannin, verapamil, tranexamic acid and derivatives thereof; various crude drug extracts such as licorice, Chinese quince, Pyrola japonica and the like; drugs such as tocopherol acetate, glycyrrhetinic acid, glycyrrhizic acid and derivatives thereof, or salts thereof; skin-whitening agents such as vitamin C, magnesium ascorbyl phosphate, ascorbic acid glucoside, arbutin, kojic acid and the like; amino acids such as arginine and lysine and the like and derivatives thereof.

The viscosity of the cleansing composition of the present disclosure is preferably 100 mPa·s or less. When the viscosity is 100 mPa·s or less, the cleansing composition of the present disclosure can be employed suitably in a pump foamer. The viscosity can be measured with a Brookfield-type viscometer (spindle No. 7; rotation speed: 10 rpm) at 30° C.

The cleansing composition of the present disclosure has excellent cleansing capability. For example, the composition can easily remove even waterproof-type (water-resistant) cosmetics (makeup).

The cleansing composition of the present disclosure has excellent foaming ability. Thus, it is possible to improve the cleansing ability of the cleansing composition and provide the user with an excellent feel upon use.

The cleansing composition of the present disclosure can be employed in a pump foamer (foaming pump), whose nozzle is pressed into a container with the hand to thereby dispense a cleansing agent in the form of a foam, without using high-pressure gas. By foaming the cleansing composition of the present disclosure with a pump foamer, a large volume of fine foam can be formed. The formation of such foam enhances cleansing ability and can also provide an excellent feel to the user.

The composition of the present disclosure has a transparent appearance that gives a good impression to the user.

Methods for producing the cleansing composition of the present disclosure will be described. The cleansing composition of the present disclosure can be prepared according to generally known methods, without being limited to a specific method. For example, the cleansing composition can be prepared by mixing each of the aforementioned components.

EXAMPLES

Examples of the cleansing composition of the present disclosure will be described below. The cleansing composition of the present disclosure, however, is not limited to the following examples. The following examples describe examples in which the cleansing compositions of the respective test examples are employed for cleansing makeup, but the composition of the present disclosure is not limited for use with makeup. The unit employed for indicating the content by percentage of each component shown in the Tables is percent by mass (% by mass).

Cleansing compositions were prepared using the components described in Table 1. In the compositions shown in Table 2 and thereafter, the components are indicated by the respective symbols shown in Table 1.

TABLE 1

| | Components |
|---|---|
| (A) | (A1) Sodium polyoxyethylene lauryl ether sulfate (2EO-SF) |
| | (A2) Sodium acyl methyl taurate |
| (B) | (B1) Cocamidopropyl betaine |
| | (B2) Imidazolinium betaine |
| (C) | (C1) PEG-3 glyceryl isostearate (HLB: 6) *1 |
| | (C2) PEG-5 glyceryl isostearate (HLB: 8) *2 |
| | (C3) PEG-8 glyceryl isostearate (HLB: 10) *3 |
| | (C4) PEG-10 glyceryl isostearate (HLB: 10) *4 |
| | (C5) PEG-15 glyceryl isostearate (HLB: 12) *5 |
| | (C6) PEG-20 glyceryl isostearate (HLB: 13) *6 |
| | (C7) PEG-30 glyceryl isostearate (HLB: 15) *7 |
| | (C8) PEG-40 glyceryl isostearate (HLB: 15) *8 |
| (D) | (D1) Isododecane |
| | (D2) Cetyl 2-ethylhexanoate *9 |
| | (D3) Glyceryl tri-2-ethylhexanoate *10 |
| | (D4) Liquid paraffin |
| | (D5) Decamethylcyclopentasiloxane *11 |
| | (D6) Ethylhexyl palmitate *12 |
| | (D7) Pentaerythritol tetra(2-ethylhexanoate) *13 |
| (E) | (E1) Octoxyglycerin |
| | (E2) Polyglyceryl-2 laurate *14 |
| | (E3) Diethylene glycol laurate |
| | (E4) Glyceryl isooctanoate |
| | (E5) Glyceryl monooctanoate |
| | (E6) Glyceryl monodecanoate |
| | (E7) Diglyceryl monooctanoate *15 |
| | (E8) Diglyceryl monodecanoate *16 |
| (F) | Ion-exchanged water |

*1: EMALEX (registered trademark) GWIS-103 (Nihon Emulsion Co., Ltd.)
*2: EMALEX (registered trademark) GWIS-105 (Nihon Emulsion Co., Ltd.)
*3: EMALEX (registered trademark) GWIS-108 (Nihon Emulsion Co., Ltd.)
*4: EMALEX (registered trademark) GWIS-110 (Nihon Emulsion Co., Ltd.)
*5: EMALEX (registered trademark) GWIS-115 (Nihon Emulsion Co., Ltd.)
*6: EMALEX (registered trademark) GWIS-120 (Nihon Emulsion Co., Ltd.)
*7: EMALEX (registered trademark) GWIS-130 (Nihon Emulsion Co., Ltd.)
*8: EMALEX (registered trademark) GWIS-140 (Nihon Emulsion Co., Ltd.)
*9: NIKKOL (registered trademark) CIO (Nikko Chemicals Co., Ltd.)
*10: RA-G-308 (Nippon Fine Chemical Co., Ltd.)
*11: Execol D-5 (Shin-Etsu Chemical Co., Ltd.)
*12: Salacos (registered trademark) P-8 (Nisshin Oillio Group, Ltd.)
*13: RA-PE408 (Nippon Fine Chemical Co., Ltd.)
*14: Sunsoft (registered trademark) Q-12D (Taiyo Kagaku Co., Ltd.)
*15: Sunsoft (registered trademark) Q-8D (Taiyo Kagaku Co., Ltd.)
*16: Sunsoft (registered trademark) Q-10D (Taiyo Kagaku Co., Ltd.)

Test Examples 1 to 32

For each composition, cleansing ability and foaming ability were evaluated. Additionally, for each composition, appearance stability and foam quality by a pump foamer were evaluated. The evaluation criteria for the items to be evaluated are as described below. The compositions and evaluation results of the compositions according to the respective Test Examples 1 to 32 are shown in Tables 2 to 9.

Cleansing Ability (Cleansing Effect):

Seven expert panelists had their faces made up with waterproof-type oily foundation and lipstick. After an hour from makeup, 2 g of the dispensed cleansing composition was applied to the panelist's face and mixed with the foundation and lipstick. Then, the foundation and lipstick were rinsed off together with the cleansing composition by using tap water. The cleansing ability of each cleansing composition was evaluated depending on how many of the seven expert panelists felt that the foundation and lipstick were removed sufficiently. The evaluation criteria are as follows.

A: Six to seven panelists evaluated that the makeup was removed sufficiently.

B: Four to five panelists evaluated that the makeup was removed sufficiently.

C: Two to three panelists evaluated that the makeup was removed sufficiently.

D: Zero to one panelist evaluated that the makeup was removed sufficiently.

Foam Durability (Foam Stability):

Seven expert panelists had their faces made up with waterproof-type oily foundation. After an hour from makeup, 2 g of the dispensed cleansing composition was applied to the panelist's face and mixed with the foundation. Evaluation was made on the foaming ability at the time of rinsing off the foundation together with the cleansing composition by using tap water. The foam durability of each cleansing composition was evaluated depending on how many of the seven expert panelists felt that the composition foamed sufficiently. The evaluation criteria are as follows.

A: Six to seven panelists evaluated that the composition foamed sufficiently.

B: Four to five panelists evaluated that the composition foamed sufficiently.

C: Two to three panelists evaluated that the composition foamed sufficiently.

D: Zero to one panelist evaluated that the composition foamed sufficiently.

Appearance Stability:

The appearance of each cleansing composition was observed, and the appearance stability of each cleansing composition was evaluated according to the following evaluation criteria.

A: The cleansing composition is transparent.

B and C: Not used for evaluation.

D: The cleansing composition is translucent or clouded.

Foam Quality:

By employing a pump foamer capable of dispensing a cleansing composition in a foamed state, each cleansing composition was dispensed from the pump foamer. The foam quality of each cleansing composition was evaluated depending on how many of the seven expert panelists evaluated that the foam dispensed from the pump foamer was fine and the volume thereof was sufficient. The pump foamer used was of a type used for commercially available hand soaps etc., wherein foam is dispensed by pressing a movable nozzle from above into a container with the hand.

A: Six to seven panelists evaluated that the dispensed foam was fine and the volume thereof was sufficient.

B: Four to five panelists evaluated that the dispensed foam was fine and the volume thereof was sufficient.

C: Two to three panelists evaluated that the dispensed foam was fine and the volume thereof was sufficient.

D: Zero to one panelist evaluated that the dispensed foam was fine and the volume thereof was sufficient.

Test Examples 1 to 3

The composition and evaluation of each of the compositions according to the respective Test Examples 1 to 3 are shown in Table 2. In Test Examples 1 to 3, the content by percentage of each of (A) the anionic surfactant and (B) the amphoteric surfactant was varied. The anionicity ratio was kept constant.

In Test Example 1, the composition was opaque, and thus, good appearance stability could not be achieved. No other evaluation was performed for Test Example 1. In Test Examples 2 and 3, all of the evaluation items were able to achieve ratings of B or higher. Thus, it is considered that the content by percentage of the anionic surfactant is preferably 2% by mass or greater, more preferably 3% by mass or greater, even more preferably 4% by mass or greater. Also, it is considered that the content by percentage of the amphoteric surfactant is preferably 1% by mass or greater, more preferably 1.5% by mass or greater, even more preferably 2% by mass or greater.

TABLE 2

| Test Examples | 1 | 2 | 3 |
|---|---|---|---|
| (A1) | 1.9 | 3.8 | 4.7 |
| (B1) | 0.9 | 1.8 | 2.3 |
| (C3) | 7 | 7 | 7 |
| (D1) | 1 | 1 | 1 |
| (E1) | 2 | 2 | 2 |
| (F) | balance | balance | balance |
| Total | 100 | 100 | 100 |
| Ionicity ratio | 0.26 | 0.41 | 0.47 |
| Anionicity ratio | 0.68 | 0.68 | 0.68 |
| Evaluation Cleansing ability | — | B | B |
| Foam durability | — | B | B |
| Appearance stability | D | A | A |
| Foam quality | — | A | B |

Test Examples 4 and 5

The composition and evaluation of each of the compositions according to the respective Test Examples 4 and 5 are shown in Table 3. In Test Example 4, the anionic surfactant (A) used was different from that in Test Examples 1 to 3. In Test Example 5, the amphoteric surfactant (B) used was different from that in Test Examples 1 to 3.

Both Test Examples 4 and 5 were able to achieve ratings comparable to or better than those of Test Examples 2 and 3. It is thus considered that the compositions of the present disclosure are less likely to be affected by the types of anionic surfactants and amphoteric surfactants.

TABLE 3

| Test Examples | 4 | 5 |
|---|---|---|
| (A1) | — | 9.5 |
| (A2) | 10.5 | — |
| (B1) | 4.5 | — |
| (B2) | — | 4.5 |
| (C3) | 7 | 7 |
| (D1) | 1 | 1 |
| (E1) | 2 | 2 |
| (F) | balance | balance |
| Total | 100 | 100 |
| Ionicity ratio | 0.65 | 0.64 |
| Anionicity ratio | 0.70 | 0.68 |
| Evaluation Cleansing ability | B | B |
| Foam durability | A | B |
| Appearance stability | A | A |
| Foam quality | A | B |

Test Examples 6 and 7

The composition and evaluation of each of the compositions according to the respective Test Examples 6 and 7 are shown in Table 4. In Test Examples 6 and 7, the content by percentage of the nonionic surfactant (C) was varied from that in the aforementioned test examples.

Test Example 6 could not achieve good cleansing ability. The composition according to Test Example 6, in which the content by percentage of the nonionic surfactant was lower, had poorer cleansing ability than the composition according to Test Example 7. Test Example 6 also had poorer foam quality. In contrast, Test Example 7 was able to achieve good cleansing ability and foam quality. It is thus considered that the content by percentage of the nonionic surfactant is preferably 2.5% by mass or greater, more preferably 3% by mass or greater.

TABLE 4

| Test Examples | 6 | 7 |
|---|---|---|
| (A1) | 9.5 | 9.5 |
| (B1) | 4.5 | 4.5 |
| (C3) | 2 | 3 |
| (D1) | 1 | 1 |
| (E1) | 2 | 2 |
| (F) | balance | balance |
| Total | 100 | 100 |
| Ionicity ratio | 0.82 | 0.78 |
| Anionicity ratio | 0.68 | 0.68 |
| Evaluation Cleansing ability | D | B |
| Foam durability | B | B |
| Appearance stability | A | A |
| Foam quality | D | A |

Test Examples 8 to 15

The composition and evaluation of each of the compositions according to the respective Test Examples 8 to 15 are shown in Table 5. In Test Examples 8 to 15, the types of nonionic surfactants were varied so that the hydrophilicities of the nonionic surfactants (C) (HLB of the nonionic surfactants (C)) differed from that of the aforementioned test examples.

Good appearance stability could not be achieved with Test Example 8 using a nonionic surfactant having a HLB of 6 and Test Example 9 using a nonionic surfactant having an HLB of 8. No other evaluation was performed for Test Example 8. Test Example 9 had insufficient cleansing ability and foam durability, whereas Test Examples 10 to 13 using nonionic surfactants having a HLB of from 10 to 13 were able to achieve sufficient cleansing ability and foam durability. Test Examples 10 to 13 also had good appearance stability and foam quality. It is thus considered that the HLB of the nonionic surfactant is preferably 9 or greater, more preferably 10 or greater. In contrast, Test Examples 14 and 15 using nonionic surfactants having an HLB of 15 could not achieve sufficient cleansing ability and foam quality. It is thus considered that the HLB of the nonionic surfactant is preferably 14 or less, more preferably 13 or less.

TABLE 5

| | Test Examples | | | | | | | |
|---|---|---|---|---|---|---|---|---|
| | 8 | 9 | 10 | 11 | 12 | 13 | 14 | 15 |
| (A1) | 9.5 | 9.5 | 9.5 | 9.5 | 9.5 | 9.5 | 9.5 | 9.5 |
| (B1) | 4.5 | 4.5 | 4.5 | 4.5 | 4.5 | 4.5 | 4.5 | 4.5 |
| (C1) | 7 | — | — | — | — | — | — | — |
| (C2) | — | 7 | — | — | — | — | — | — |

TABLE 5-continued

|  | Test Examples | | | | | | | |
|---|---|---|---|---|---|---|---|---|
|  | 8 | 9 | 10 | 11 | 12 | 13 | 14 | 15 |
| (C3) | — | — | 7 | — | — | — | — | — |
| (C4) | — | — | — | 7 | — | — | — | — |
| (C5) | — | — | — | — | 7 | — | — | — |
| (C6) | — | — | — | — | — | 7 | — | — |
| (C7) | — | — | — | — | — | — | 7 | — |
| (C8) | — | — | — | — | — | — | — | 7 |
| (D1) | 1 | 1 | 1 | 1 | 1 | 1 | 1 | 1 |
| (E1) | 2 | 2 | 2 | 2 | 2 | 2 | 2 | 2 |
| (F) | balance | balance | balance | balance | balance | balance | balance | balance |
| Total | 100 | 100 | 100 | 100 | 100 | 100 | 100 | 100 |
| Ionicity ratio | 0.64 | 0.64 | 0.64 | 0.64 | 0.64 | 0.64 | 0.64 | 0.64 |
| Anionicity ratio | 0.68 | 0.68 | 0.68 | 0.68 | 0.68 | 0.68 | 0.68 | 0.68 |
| Evaluation Cleansing ability | — | C | B | B | B | B | C | C |
| Foam durability | — | C | B | B | B | B | B | B |
| Appearance stability | D | D | A | A | A | A | A | A |
| Foam quality | — | D | B | A | B | B | C | D |

Test Examples 16 to 19

The composition and evaluation of each of the compositions according to the respective Test Examples 16 to 19 are shown in Table 6. In Test Examples 16 to 19, the content by percentage of the oily component (D) was varied from that in the aforementioned test examples.

Test Example 16, in which the content by percentage of the oily component was 0.1% by mass, could not achieve sufficient cleansing ability. In contrast, Test Examples 17 and 18, in which the content by percentage of the oily component was 0.3% by mass and 4% by mass respectively, were able to achieve sufficient cleansing ability. It is thus considered that the content by percentage of the oily component is preferably 0.2% by mass or greater, more preferably 0.5% by mass or greater, even more preferably 1% by mass or greater.

Test Example 19, in which the content by percentage of the oily component was 6% by mass, could not achieve sufficient foam durability. In contrast, Test Examples 17 and 18 were able to achieve sufficient foam durability. It is thus considered that the content by percentage of the oily component is preferably 5% by mass or less, more preferably 4% by mass or less.

TABLE 6

| Test Examples | 16 | 17 | 18 | 19 |
|---|---|---|---|---|
| (A1) | 9.5 | 9.5 | 9.5 | 9.5 |
| (B1) | 4.5 | 4.5 | 4.5 | 4.5 |
| (C3) | 7 | 7 | 7 | 7 |

TABLE 6-continued

| Test Examples | 16 | 17 | 18 | 19 |
|---|---|---|---|---|
| (D1) | 0.1 | 0.3 | 4 | 6 |
| (E1) | 2 | 2 | 2 | 2 |
| (F) | balance | balance | balance | balance |
| Total | 100 | 100 | 100 | 100 |
| Ionicity ratio | 0.66 | 0.66 | 0.56 | 0.52 |
| Anionicity ratio | 0.68 | 0.68 | 0.68 | 0.68 |
| Evaluation Cleansing ability | C | B | B | B |
| Foam durability | B | B | B | C |
| Appearance stability | A | A | A | A |
| Foam quality | D | B | B | C |

Test Examples 20 to 26

The composition and evaluation of each of the compositions according to the respective Test Examples 20 to 26 are shown in Table 7. In Test Examples 20 to 26, the types of the oily component (D) were varied from that in the aforementioned test examples.

All of Test Examples 20 to 26 were able to achieve sufficient cleansing ability and foam durability. It is thus considered that the cleansing ability and foam durability of the composition are less likely to be affected by the type of the oily component.

Test Examples 22 to 26 had better foam quality than Test Examples 20 and 21. It is thus considered that it is preferred to use the oily components (D3) to (D7) in cases of employing the cleansing composition in a pump foamer.

TABLE 7

|  | Test Examples | | | | | | |
|---|---|---|---|---|---|---|---|
|  | 20 | 21 | 22 | 23 | 24 | 25 | 26 |
| (A1) | 9.5 | 9.5 | 9.5 | 9.5 | 9.5 | 9.5 | 9.5 |
| (B1) | 4.5 | 4.5 | 4.5 | 4.5 | 4.5 | 4.5 | 4.5 |
| (C3) | 7 | 7 | 7 | 7 | 7 | 7 | 7 |
| (D1) | 1 | — | — | — | — | — | — |
| (D2) | — | 1 | — | — | — | — | — |
| (D3) | — | — | 1 | — | — | — | — |
| (D4) | — | — | — | 1 | — | — | — |

TABLE 7-continued

| | Test Examples | | | | | | |
|---|---|---|---|---|---|---|---|
| | 20 | 21 | 22 | 23 | 24 | 25 | 26 |
| (D5) | — | — | — | — | 1 | — | — |
| (D6) | — | — | — | — | — | 1 | — |
| (D7) | — | — | — | — | — | — | 1 |
| (E1) | 2 | 2 | 2 | 2 | 2 | 2 | 2 |
| (F) | balance | balance | balance | balance | balance | balance | balance |
| Total | 100 | 100 | 100 | 100 | 100 | 100 | 100 |
| Ionicity ratio | 0.64 | 0.64 | 0.64 | 0.64 | 0.64 | 0.64 | 0.64 |
| Anionicity ratio | 0.68 | 0.68 | 0.68 | 0.68 | 0.68 | 0.68 | 0.68 |
| Evaluation Cleansing ability | B | B | B | B | B | B | B |
| Foam durability | B | B | B | B | B | B | B |
| Appearance stability | A | A | A | A | A | A | A |
| Foam quality | B | B | A | A | A | A | A |

Test Examples 27 to 29

The composition and evaluation of each of the compositions according to the respective Test Examples 27 to 29 are shown in Table 8. In Test Examples 27 to 29, the content by percentage of the foaming agent (E) was varied from that in the aforementioned test examples.

Test Example 27 including no foaming agent and Test Example 28 including 0.3% by mass of the foaming agent had poor cleansing ability and foam durability. In contrast, Test Example 29 including 0.5% by mass of the foaming agent was able to achieve sufficient cleansing ability and foam durability. It is thus considered that the content by percentage of the foaming agent is preferably 0.4% by mass or greater, more preferably 0.5% by mass or greater, even more preferably 1% by mass or greater.

TABLE 8

| | Test Examples | 27 | 28 | 29 |
|---|---|---|---|---|
| (A1) | | 9.5 | 9.5 | 9.5 |
| (B1) | | 4.5 | 4.5 | 4.5 |
| (C3) | | 7 | 7 | 7 |
| (D1) | | 1 | 1 | 1 |
| (E1) | | — | 0.3 | 0.5 |
| (F) | | balance | balance | balance |
| Total | | 100 | 100 | 100 |
| Ionicity ratio | | 0.64 | 0.64 | 0.64 |
| Anionicity ratio | | 0.68 | 0.68 | 0.68 |
| Evaluation | Cleansing ability | D | C | B |
| | Foam durability | C | C | B |
| | Appearance stability | A | A | A |
| | Foam quality | B | B | B |

Test Examples 30 to 32

The composition and evaluation of each of the compositions according to the respective Test Examples 30 to 32 are shown in Table 9. In Test Examples 30 to 32, the types of the foaming agent (E) were varied from that in the aforementioned test examples.

Test Example 30 including a compound represented by the aforementioned Chem. 5 could not achieve sufficient foam durability and foam quality. Test Example 31 employing a polyethylene glycol fatty acid ester had insufficient cleansing ability, foam durability, and foam quality. It is thus considered that the components (E2) and (E3) have a poor function/effect as foaming agents. In contrast, Test Example 32 was able to achieve good results in all evaluation items. It is thus considered that, with consideration given also to Test Examples 10 and 20, the components (E1) and (E4) are preferable as foaming agents.

TABLE 9

| | Test Examples | 30 | 31 | 32 |
|---|---|---|---|---|
| (A1) | | 9.5 | 9.5 | 9.5 |
| (B1) | | 4.5 | 4.5 | 4.5 |
| (C3) | | 7 | 7 | 7 |
| (D1) | | 1 | 1 | 1 |
| (E2) | | 2 | — | — |
| (E3) | | — | 2 | — |
| (E4) | | — | — | 2 |
| (F) | | balance | balance | balance |
| Total | | 100 | 100 | 100 |
| Ionicity ratio | | 0.64 | 0.64 | 0.64 |
| Anionicity ratio | | 0.68 | 0.68 | 0.68 |
| Evaluation | Cleansing ability | B | C | B |
| | Foam durability | C | C | B |
| | Appearance stability | B | A | A |
| | Foam quality | C | C | B |

Test Examples 33 to 52

The same tests as those for Test Examples 1 to 32 were performed. The test methods were the same as those for Test Examples 1 to 32. The evaluation methods were the same as those for Test Examples 1 to 32, except that there were five expert panelists and the following evaluation criteria were employed.

Cleansing Ability:

A: Four to five panelists evaluated that the makeup was removed sufficiently.

B: Not used for evaluation.

C: Two to three panelists evaluated that the makeup was removed sufficiently.

D: Zero to one panelist evaluated that the makeup was removed sufficiently.

Foam Durability:

A: Four to five panelists evaluated that the composition foamed sufficiently.

B: Not used for evaluation.

C: Two to three panelists evaluated that the composition foamed sufficiently.

D: Zero to one panelist evaluated that the composition foamed sufficiently.

Appearance Stability:

The appearance of each cleansing composition was observed, and the appearance stability of each cleansing composition was evaluated according to the following evaluation criteria.

A: The cleansing composition is transparent.

B and C: Not used for evaluation.

D: The cleansing composition is translucent or clouded.

Foam Quality:

A: Four to five panelists evaluated that the dispensed foam was fine and the volume thereof was sufficient.

B: Not used for evaluation.

C: Two to three panelists evaluated that the dispensed foam was fine and the volume thereof was sufficient.

D: Zero to one panelist evaluated that the dispensed foam was fine and the volume thereof was sufficient.

Test Examples 33 to 42

The composition and evaluation of each of the compositions according to the respective Test Examples 33 to 42 are shown in Tables 10 and 11. In Test Examples 33 to 42, the content by percentage of each of the components (A) to (D) was varied so as to vary the ionicity ratio. The anionicity ratio was kept constant.

Test Example 33 could not achieve sufficient cleansing ability. In contrast, Test Examples 34 to 42 were able to achieve sufficient cleansing ability. It is thus considered that the ionicity ratio is preferably 0.9 or less.

Test Examples 39 to 42 could not achieve sufficient foam durability. In contrast, Test Examples 33 to 38 were able to achieve sufficient foam durability. It is thus considered that the ionicity ratio is preferably 0.35 or greater, more preferably 0.4 or greater. Further, Test Examples 39 to 42 could not achieve sufficient foam quality. It is thus considered that the ionicity ratio is preferably 0.35 or greater, also from the viewpoint of improving foam quality.

TABLE 10

| | | Test Examples | | | | |
|---|---|---|---|---|---|---|
| | | 33 | 34 | 35 | 36 | 37 |
| (A1) | | 18.0 | 17.0 | 15.1 | 13.2 | 11.3 |
| (B1) | | 8.6 | 8.1 | 7.2 | 6.3 | 5.4 |
| (C3) | | 1.5 | 3 | 6 | 9 | 12 |
| (D1) | | 0.5 | 1 | 2 | 3 | 4 |
| (E1) | | 1 | 1 | 1 | 1 | 1 |
| (F) | | balance | balance | balance | balance | balance |
| Total | | 100 | 100 | 100 | 100 | 100 |
| Ionicity ratio | | 0.93 | 0.86 | 0.74 | 0.62 | 0.51 |
| Anionicity ratio | | 0.68 | 0.68 | 0.68 | 0.68 | 0.68 |
| Evaluation | Cleansing ability | D | A | A | A | A |
| | Foam durability | A | A | A | A | A |
| | Appearance stability | A | A | A | A | A |
| | Foam quality | A | A | A | A | A |

TABLE 11

| | | Test Examples | | | | |
|---|---|---|---|---|---|---|
| | | 38 | 39 | 40 | 41 | 42 |
| (A1) | | 9.5 | 7.6 | 5.7 | 3.8 | 1.9 |
| (B1) | | 4.5 | 3.6 | 2.7 | 1.8 | 0.9 |
| (C3) | | 15 | 18 | 21 | 24 | 27 |
| (D1) | | 5 | 6 | 7 | 8 | 9 |
| (E1) | | 1 | 1 | 1 | 1 | 1 |
| (F) | | balance | balance | balance | balance | balance |
| Total | | 100 | 100 | 100 | 100 | 100 |
| Ionicity ratio | | 0.41 | 0.32 | 0.23 | 0.15 | 0.07 |
| Anionicity ratio | | 0.68 | 0.68 | 0.68 | 0.68 | 0.68 |
| Evaluation | Cleansing ability | A | A | A | A | A |
| | Foam durability | A | C | D | D | D |
| | Appearance stability | A | A | A | A | A |
| | Foam quality | A | C | D | D | D |

Test Examples 43 to 52

The composition and evaluation of each of the compositions according to the respective Test Examples 43 to 52 are shown in Tables 12 and 13. In Test Examples 43 to 52, the content by percentage of each of (A) the anionic surfactant and (B) the amphoteric surfactant was varied so as to vary the anionicity ratio. The ionicity ratio was kept substantially constant.

Test Example 43 could achieve neither cleansing ability nor sufficient foam durability. In contrast, Test Examples 44 to 51 were able to achieve sufficient cleansing ability and foam durability. It is thus considered that the anionicity ratio is preferably 0.1 or greater, more preferably 0.15 or greater.

Test Example 52 could achieve neither foam durability, appearance stability, nor foam quality. In contrast, Test Examples 44 to 51 were rated favorably in all of the evaluation items. It is thus considered that the anionicity ratio is preferably 0.9 or less.

TABLE 12

| | | Test Examples | | | | |
|---|---|---|---|---|---|---|
| | | 43 | 44 | 45 | 46 | 47 |
| (A1) | | 1.9 | 3.8 | 5.7 | 7.6 | 9.5 |
| (B1) | | 18.9 | 16.8 | 14.7 | 12.6 | 10.5 |
| (C3) | | 9 | 9 | 9 | 9 | 9 |
| (D1) | | 3 | 3 | 3 | 3 | 3 |
| (E1) | | 1 | 1 | 1 | 1 | 1 |
| (F) | | balance | balance | balance | balance | balance |
| Total | | 100 | 100 | 100 | 100 | 100 |
| Ionicity ratio | | 0.63 | 0.63 | 0.63 | 0.63 | 0.62 |
| Anionicity ratio | | 0.09 | 0.18 | 0.28 | 0.38 | 0.47 |
| Evaluation | Cleansing ability | D | A | A | A | A |
| | Foam durability | C | A | A | A | A |
| | Appearance stability | A | A | A | A | A |
| | Foam quality | C | A | A | A | A |

TABLE 13

|  |  | Test Examples | | | | |
|---|---|---|---|---|---|---|
|  |  | 48 | 49 | 50 | 51 | 52 |
|  | (A1) | 11.3 | 13.2 | 15.1 | 17.0 | 18.0 |
|  | (B1) | 8.4 | 6.3 | 4.2 | 2.1 | 1.1 |
|  | (C3) | 9 | 9 | 9 | 9 | 9 |
|  | (D1) | 3 | 3 | 3 | 3 | 3 |
|  | (E1) | 1 | 1 | 1 | 1 | 1 |
|  | (F) | balance | balance | balance | balance | balance |
|  | Total | 100 | 100 | 100 | 100 | 100 |
|  | Ionicity ratio | 0.62 | 0.62 | 0.62 | 0.61 | 0.61 |
|  | Anionicity ratio | 0.57 | 0.68 | 0.78 | 0.89 | 0.94 |
| Evaluation | Cleansing ability | A | A | A | A | A |
|  | Foam durability | A | A | A | A | D |
|  | Appearance stability | A | A | A | A | D |
|  | Foam quality | A | A | A | A | D |

From Test Examples 1 to 52, it is considered that the content by percentage of the anionic surfactant is preferably 17.5% by mass or less, more preferably 17% by mass or less. Further, it is considered that the content by percentage of the amphoteric surfactant is preferably 17.5% by mass or less, more preferably 17% by mass or less. Further, it is considered that the content by percentage of the nonionic surfactant is preferably 17% by mass or less, more preferably 15% by mass or less. Further, it is considered that, in cases where the ionicity ratio is 0.8 or greater, the content by percentage of the nonionic surfactant may be 2.5% by mass or greater, preferably 3% by mass or greater.

Test Examples 53 to 56

The composition and evaluation of each of the compositions according to the respective Test Examples 53 to 56 are shown in Table 14. The evaluation criteria were the same as those for Test Examples 1 to 32. In Test Examples 53 to 56, the number of carbon atoms in the acyl group in each foaming agent component (E) was varied.

Test Example 53, which employed a monoglycerin ester including an acyl group having eight carbon atoms in the compound represented by the aforementioned Chem. 6, was able to achieve sufficient ratings in all of the evaluation items. Similarly, Test Example 10, which employed a monoglyceryl ether including an alkyl group having eight carbon atoms, achieved good results. In contrast, Test Example 54, which employed a monoglycerin ester having ten carbon atoms, yielded an opaque composition and had insufficient cleansing ability, foam durability, and foam quality. It is thus considered that the number of carbon atoms in the acyl group and alkyl group in the compound represented by Chem. 6 is preferably 8 or less.

Test Examples 55 and 56, which employed diglycerin esters including an acyl group having eight and ten carbon atoms, respectively, in the compound represented by the aforementioned Chem. 5, could not achieve sufficient foam durability and foam quality. The result was the same for Test Example 30, which employed a diglycerin ester including an acyl group having twelve carbon atoms. It is thus considered that diglycerin esters having eight or more carbon atoms do not function as foaming agents but impair foaming ability.

TABLE 14

|  | Test Examples | 53 | 54 | 55 | 56 |
|---|---|---|---|---|---|
|  | (A1) | 9.5 | 9.5 | 9.5 | 9.5 |
|  | (B1) | 4.5 | 4.5 | 4.5 | 4.5 |
|  | (C3) | 7 | 7 | 7 | 7 |
|  | (D1) | 1 | 1 | 1 | 1 |
|  | (E5) | 2 | — | — | — |
|  | (E6) | — | 2 | — | — |
|  | (E7) | — | — | 2 | — |
|  | (E8) | — | — | — | 2 |
|  | (F) | balance | balance | balance | balance |
|  | Total | 100 | 100 | 100 | 100 |
|  | Ionicity ratio | 0.64 | 0.64 | 0.64 | 0.64 |
|  | Anionicity ratio | 0.68 | 0.68 | 0.68 | 0.68 |
| Evaluation | Cleansing ability | B | C | B | B |
|  | Foam durability | B | C | C | C |
|  | Appearance stability | B | D | B | B |
|  | Foam quality | B | C | C | C |

The cleansing composition of the invention has been described according to the foregoing embodiments and examples, but the invention is not limited to the foregoing embodiments and examples and may encompass various transformations, modifications, and improvements made to the various disclosed elements (including elements disclosed in the Claims, Description, and Drawings) within the scope of the invention and according to the fundamental technical idea of the present invention. Further, various combinations, substitutions, and selections of the various disclosed elements are possible within the scope of the claims of the invention.

Further issues, objectives, and embodiments (including modifications) of the present invention are revealed also from the entire disclosure of the invention including the Claims.

The numerical ranges disclosed herein are to be construed in such a manner that arbitrary numerical values and ranges falling within the disclosed ranges are treated as being concretely described herein, even where not specifically stated.

Some or all of the foregoing embodiments may be described as in the following additional features, although not limited thereto. The various additional features may be employed in combination with the claim(s) in the Scope of Claims.

{Additional Feature 1}
A cleansing composition comprising:
(A) 2 to 17% by mass of an anionic surfactant;
(B) 2 to 17% by mass of an amphoteric surfactant;
(C) 4 to 17% by mass of a nonionic surfactant; and
(D) 0.2 to 5% by mass of an oily component; and
not comprising a substantial amount of a compound represented by the aforementioned Chem. 4 or Chem. 5.

{Additional Feature 2}
A cleansing composition comprising:
(A) 2 to 17.5% by mass of an anionic surfactant;
(B) 1 to 17.5% by mass of an amphoteric surfactant;
(C) 4 to 17% by mass of a nonionic surfactant; and
(D) 0.2 to 5% by mass of an oily component; and
not comprising a substantial amount of a compound represented by the aforementioned Chem. 4 or Chem. 5.

{Additional Feature 3}
A cleansing composition comprising:
(A) 2 to 17.5% by mass of an anionic surfactant;
(B) 1 to 17.5% by mass of an amphoteric surfactant;
(C) 2.5 to 17% by mass of a nonionic surfactant; and
(D) 0.2 to 5% by mass of an oily component;

wherein:
the ratio of the total mass of the component (A) and the component (B) to the total mass of the component (A), the component (B), the component (C), and the component (D) is from 0.8 to 0.9; and
the cleansing composition does not comprise a substantial amount of a compound represented by the aforementioned Chem. 4 or Chem. 5.

{Additional Feature 4}

The cleansing composition as set forth in any one of the aforementioned additional features, wherein the ratio of the total mass of the component (A) and the component (B) to the total mass of the component (A), the component (B), the component (C), and the component (D) is from 0.4 to 0.9.

INDUSTRIAL APPLICABILITY

The cleansing composition of the present disclosure can be used suitably for cleansing the skin. Particularly, the composition of the present disclosure can be employed suitably for cleansing to remove makeup on the skin. The composition of the present disclosure can be employed suitably as contents to be placed in a pump foamer.

The invention claimed is:

1. A cleansing composition, comprising:
(A) 2 to 17.5% by mass of an anionic surfactant,
(B) 1 to 17.5% by mass of an amphoteric surfactant,
(C) 2.5 to 17% by mass of a nonionic surfactant having an HLB of 9 to 14,
(D) 0.2 to 5% by mass of an oily component, and
(E) 0.4 to 5% by mass of a foaming agent;
wherein the cleansing composition comprises no amount of a compound having structure

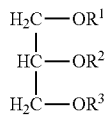

wherein any one of $R^1$, $R^2$, and $R^3$ is an alkyl group or acyl group having nine or more carbon atoms, and the other two are hydrogen atoms;
wherein the cleansing composition comprises no amount of a compound having structure

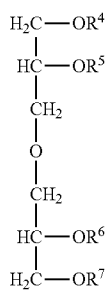

wherein any one of $R^4$, $R^5$, $R^6$, and $R^7$ is an alkyl group or acyl group having eight or more carbon atoms, and the other three are hydrogen atoms;
wherein the component (E) includes at least one compound having structure

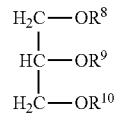

wherein any one of $R^3$, $R^9$, and $R^{10}$ is an alkyl group or acyl group having eight or fewer carbon atoms, and the other two are hydrogen atoms;
wherein the component (C) is a polyoxyethylene glyceryl fatty acid ester;
wherein the ratio of the mass of the component (A) to the total mass of the component (A) and the component (B) is in the range of 0.1 to 0.9; and
wherein the ratio of the total mass of the component (A) and the component (B) to the total mass of the component (A), the component (B), the component (C), and the component (D) is in the range of 0.35 to 0.9.

2. The cleansing composition, according to claim 1, further comprising:
(F) 60 to 85% by mass of water.

3. The cleansing composition, according to claim 1, wherein the component (A) is selected from the group consisting of polyoxyethylene alkyl ether sulfates and acyl methyl taurates.

4. The cleansing composition, according to claim 1, wherein the component (B) is a betaine surfactant.

5. The cleansing composition, according to claim 1, wherein:
the cleansing composition includes no bicontinuous phase.

6. The cleansing composition, according to claim 1, wherein:
the cleansing composition is applicable using a foaming pump without a high-pressure gas.

7. The cleansing composition, according to claim 1, wherein:
the cleansing composition is used as a makeup cleansing agent.

* * * * *